United States Patent [19]
Graham et al.

[11] Patent Number: 5,549,700
[45] Date of Patent: Aug. 27, 1996

[54] SEGMENTED PROSTHETIC ARTICULATION

[75] Inventors: John W. Graham, Cincinnati; Timothy McTighe, Chagrin Falls; Paul Mraz, University Heights, all of Ohio

[73] Assignee: Ortho Development Corporation, Draper, Utah

[21] Appl. No.: 362,804

[22] Filed: Dec. 21, 1994

Related U.S. Application Data

[63] Continuation-in-part of Ser. No. 117,388, Sep. 7, 1993, abandoned.

[51] Int. Cl.$^6$ .................................. A61F 2/34; A61F 2/36
[52] U.S. Cl. ........................ 623/22; 623/23; 403/133; 403/135
[58] Field of Search .......................... 623/19, 20, 22, 623/23; 403/133, 135

[56] References Cited

U.S. PATENT DOCUMENTS

| | | |
|---|---|---|
| 3,521,302 | 7/1970 | Muller ............................ 623/22 X |
| 3,723,995 | 4/1973 | Baumann . |
| 3,740,769 | 6/1973 | Haboush ............................ 623/22 |
| 3,806,960 | 4/1974 | Weber . |
| 3,894,297 | 7/1975 | Mittelmeier et al. . |
| 3,924,275 | 12/1975 | Heimke et al. . |
| 3,978,528 | 9/1976 | Crep . |
| 4,666,450 | 5/1987 | Kenna . |
| 4,778,474 | 10/1988 | Homsy . |
| 4,840,630 | 6/1989 | Kitamura . |
| 4,840,631 | 6/1989 | Mathys ............................ 623/22 |
| 4,894,064 | 1/1990 | Imhof . |
| 4,963,154 | 10/1990 | Anapliotis et al. . |
| 5,092,898 | 3/1992 | Beeki et al. ............................ 623/22 |
| 5,147,407 | 9/1992 | Tager . |
| 5,181,926 | 1/1993 | Koch et al. ............................ 623/22 |
| 5,188,476 | 2/1993 | Mori ............................ 403/133 |
| 5,197,987 | 3/1993 | Koch et al. . |
| 5,263,988 | 11/1993 | Huebner . |
| 5,358,525 | 10/1994 | Fox et al. ............................ 623/18 |

FOREIGN PATENT DOCUMENTS

| | | |
|---|---|---|
| 0497079 | 8/1992 | European Pat. Off. . |
| 2933174 | 10/1978 | Germany . |
| 1220717A | 2/1988 | Japan . |
| 1300949 | 5/1988 | Japan . |
| 1189325 | 4/1970 | United Kingdom ............ 623/22 |
| 1527498 | 10/1978 | United Kingdom . |
| 2126096 | 3/1984 | United Kingdom ............ 623/22 |

OTHER PUBLICATIONS

*The Use of Dense Alumina–Alumina Ceramic Combination In Total Hip Replacement* by P. Boutin, P. Christel, J. M. Dorlot, A. Meunier, A. de Roquancourt, D. Blanquaert, S. Herman, L. Sedel, and J. Witvoet, pp.1203–1232 of Journal of Biomedical Materials Research, vol. 22 (1988).

*A View Of 15 Years Results Obtained Using The Alumina–Alumina Hip Joint Prothesis* by P. Boutin, P. Christel, J. Dorlot, A. Meunier, L. Sedel and J. Witvoet, pp. 297–303 of High Tech Ceramics, Elsevier Science Publishers B. V. Amsterdam, 1987—Printed in the Netherlands.

*U.S. Clinical Experience With High Performance Ceramic Total Hip Replacement* by D. I. Bardos, pp. 305–311 of High Tech Ceramics, Elsevier Science Publishers B. V., Amsterdam, 1987—Printed in the Netherlands.

*Biomechanical Stability And Design Wear,* by I. C. Clarke, J. M. Dorlot, J. Graham, D. J. Levine, H. Oonishi, J. Rieu, D. Rigney, G. Schwartz, L. Sedel, A. Toni and J. Zitelli, pp. 1–5.

(List continued on next page.)

*Primary Examiner*—David H. Willse
*Attorney, Agent, or Firm*—Thorpe, North & Western

[57] ABSTRACT

A ball and socket prosthetic joint device. A plurality of curved rigid segments are embedded within and extend out of a polymeric cushion to form a discontinuous hemispherical bearing surface for slidable engagement with a continuous hemispherical bearing surface.

17 Claims, 3 Drawing Sheets

OTHER PUBLICATIONS

*Wear, Creep, And Frictional Heating Of Femoral Implant Articulating Surfaces And The Effect On Long Term Performances–Part II, Friction, Heating And Torque,* by J. A. Davidson, G. Schwartz and G. Lynch, pp. 69–91 of J. Biomed. Mater. Res.: Applied Biomaterials, vol. 22, No. A1 (1988).

*Bio–Clad™, The New Standard In Acetabular Cup Technology,* by BioMet Inc., published in The Journal of Bone and Joint Surgery, 1982.

*Immediate, Cementless Fixation By Direct Skeletal Attachment,* by Biomet, Inc., published in The Journal of Bone and Joint Surgery, 1984.

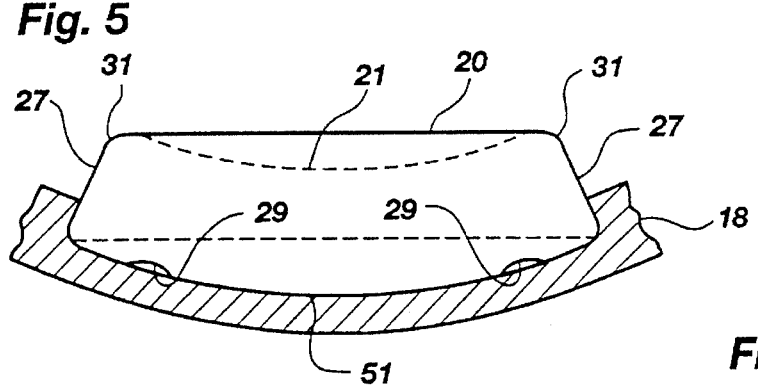
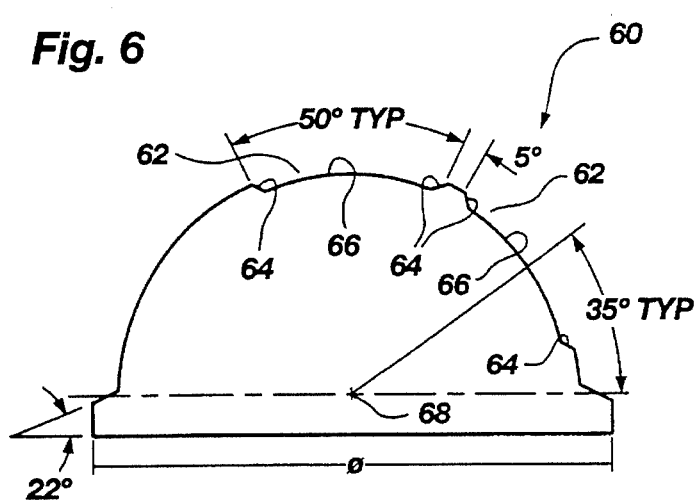
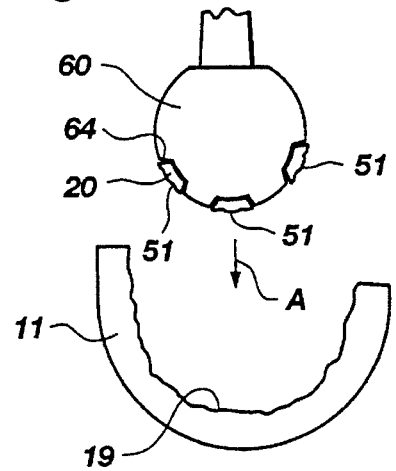
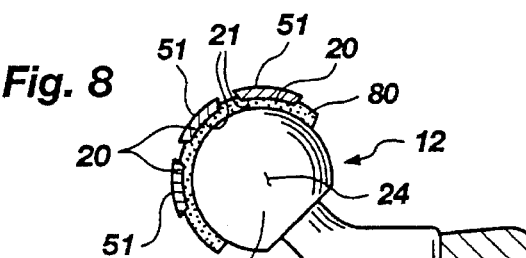
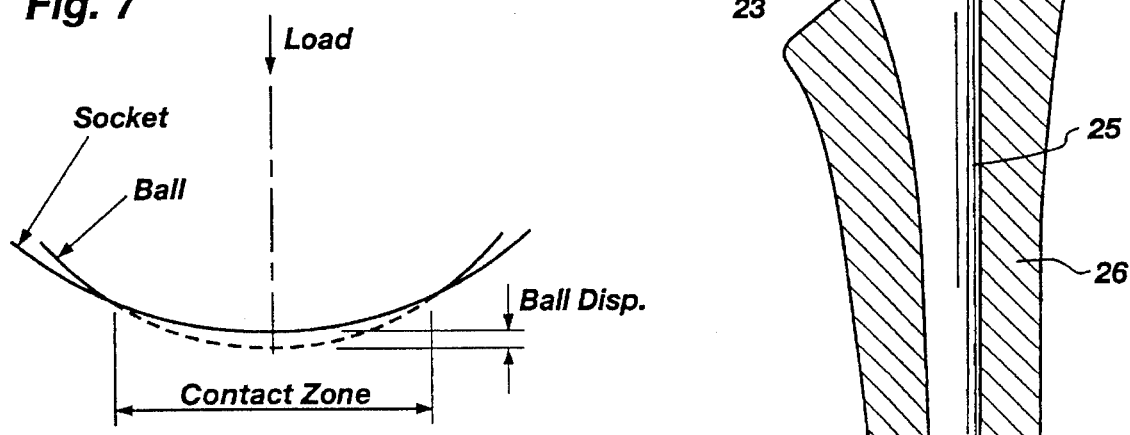

5,549,700

SEGMENTED PROSTHETIC ARTICULATION

This is a continuation-in-part of U.S. patent application Ser. No. 08/117,388, filed on Sep. 7, 1993, entitled "Prosthetic Body Joint", now abandoned.

BACKGROUND OF THE INVENTION

1. The Field of the Invention

The present invention relates generally to the field of articulating prosthetic joints for use in a human or animal body. More particularly, it concerns a socket member for use in a ball and socket prosthetic joint device such as a hip stem prosthesis.

2. The Background Art

It is known in the art to replace a joint, such as the hip joint, with an artificial hip stem replacement. Numerous artificial implants are available which can be installed to replace the natural hip joint with an artificial ball and socket combination. A passage called the medullary canal is reamed or bored in the upper end of the femur. A stem or femoral component of an artificial implant is inserted into the reamed portion of the medullary canal in a secure, seated position. A neck member extends outward and away from the stem and terminates in a spherical knob or ball for insertion into a socket member secured within the acetabulum of the hip. The ball and socket member are maintained in rotational contact with one another about the three major orthogonal axes.

Prosthetic joint implants are thus generally constructed with two bearing elements maintained in slidable contact. Such prosthetic joint implants are typically constructed of biocompatible metals, such as stainless steel (e.g., 316LC), cobalt alloys (e.g., ASTM F-75) and titanium alloys (e.g., 90% Ti, 6% Al and 4% V), ceramics (e.g., aluminum oxide, $Al_2O_3$ and zirconium oxide, $ZrO_2$), and biocompatible polymers such as ultra-high molecular weight polyethylene (UHMWPE), polyetheretherketone (PEEK), and medical grade polysulfone. Recognizing that the present invention is applicable to other joints as well, total hip replacement (THR) prostheses are discussed herein for purposes of example.

In one THR implant, a metal ball, or head, is fixed to the patient's femur by a hip stem and a UHMWPE cup is fixed to the patient's acetabulum. The metal head articulates or rides in the UHMWPE cup. Generally, to reduce friction and wear, the bearing surface of the metal head is polished and that of the UHMWPE cup is smooth. In addition, these bearing surfaces are often lubricated with synovial fluid while in the patient's body. Even so, when the polished ball articulates in the UHMWPE cup, some wear of the UHMWPE takes place. This wear generates debris in the form of submicroscopic UHMWPE particles.

Scientific studies using joint simulators have shown that the wear process in ball and socket prostheses generates hundreds of thousands of polyethylene particles with each step the patient takes. Retained lubricant from simulated hip joint testing machines have revealed literally billions of microscopic particles of the polymer cup (in simulating a one year wear cycle in a human hip). These particles tend to speed up the wear process.

Scientific studies throughout the world have shown that such high quantities of wear debris can generate a bone disease called osteolysis in patients who have had a total hip replacement prosthesis. A high incidence of osteolysis (nearly 21%) is being discovered in prosthesis implanted after five to seven years. Osteolysis destroys healthy bone but seldom causes pain, sometimes causing a bone to become susceptible to fracture before the patient knows anything is wrong. In most cases, debris resulting from wear between the metal ball and polymer cup surfaces is named as the primary cause of the disorder. Biological analysis of such damaged bone sections have established this disorder as being one of the most critical orthopaedic problems today.

Point contacts and resulting nonuniform load transfer between the ball and socket components further contribute to wear debris generation. As the contact area between the bearing surfaces decreases, the stress that is transmitted between the surfaces increases. The increased stress not only increases wear debris generation, it can also raise the possibility of fracture of one or both surfaces, especially when the stress concentration becomes highly localized.

There are other sources of wear debris in joint prostheses besides the ball and cup interface. The socket portion of many THR implants includes a two-piece cup system, with the UHMWPE cup seated in a metal shell. It has been reported that large quantities of polyethylene debris are generated between the UHMWPE cup and the metal shell. The fit between the cup and shell is typically close but not perfect. Normal walking is likely to produce sufficient movement between the cup and the shell to generate such debris. The metal shell is usually fastened directly to the patient's acetabulum bone, often with screws. The generated debris may gradually work its way out of the space between the polyethylene cup and metal shell. The debris can then migrate through the screw holes or other gaps between the metal shell and the surrounding acetabulum bone.

Prior attempts at limiting movement between the cup and shell have included forming a plurality of serrations or scallops on the inside rim of the metal shell. The cup and shell are then locked together by snap-fitting the cup into the shell, with the metal serrations or scallops locking into the outside rim of the polymeric cup. While this arrangement provides initial macro-dimensional stability between the cup and shell, the cup begins to move microscopically within the shell with time and use because of slight dimensional differences between the congruent surfaces.

OBJECTS AND SUMMARY OF THE INVENTION

It is therefore an object of the present invention to provide a prosthetic socket member which avoids developing point contacts with a corresponding spherical ball component.

It is another object of the present invention to provide such a prosthetic socket member which provides an increased amount of surface area contact with a corresponding spherical ball component.

It is a further object of the present invention to provide such a prosthetic socket member which produces a more uniform transfer of stress from the bearing surfaces through the socket member.

It is still another object of the present invention to provide such a prosthetic socket member which inhibits wear debris generation.

The above objects and others not specifically recited are realized in a specific illustrative embodiment of a prosthetic joint implant with an extended service life.

The present invention is directed to a socket component comprising a polymeric cup insert engaged within a shell such that relative movement between contacting surfaces of the cup and shell are limited so as to substantially prevent wear debris generation. Applicants have discovered that certain embodiments are particularly advantageous. One such embodiment involves molding the cup from shrinkable polymeric material. The polymer is injected directly into the shell and flows into recesses formed within the shell. Each recess includes an enlarged portion defined by an annular shoulder, causing the polymer to fill the enlargement and form an annular retaining lip seated against the shoulder. As the polymeric cup cures, the projections tend to shrink so as to impose a tensile force which engages the retaining lips tightly against the annular shoulders to thereby substantially prevent passage of particles through the holes.

Recesses can also be formed by fusing a plurality of generally spherical beads directly to the interior surface of the shell so as to form pores between the beads. The polymeric cup insert is molded directly over the fused beads and into the pores. When the polymeric cup cures, it has a plurality of tiny grips onto the spherical beads such that the cup is substantially immovably engaged with the spherical beads.

In a preferred embodiment, the recesses are located on the inside or concave surface of the shell and the polymeric material of the cup insert is actually formed into the recesses, such as by molding, casting, forging or any other suitable method. With this embodiment, the mating recesses may be actually formed into the shell itself, such as by machining or texturing its inside surface. Alternatively, the recesses may be produced by applying a porous or textured coating to the inside surface of the shell.

Surface area contact between the bearing surfaces is increased, and the propensity toward point contacts is decreased, by forming a discontinuous hemispherical bearing surface from rigid and hard bearing segments for slidable engagement with a spherical joint ball. The segments are embedded directly within the polymeric cup in a predetermined pattern and configuration, with the polymeric cup having a much lower elastic modulus than the bearing segments. Because of the lower elastic modulus of the polymeric cup, the cup flexibly contracts as loads are transmitted while the shape of the bearing surfaces remains relatively unchanged. As a particular load decreases or changes direction, a corresponding expansion of the underlying polymer occurs to push the segments outward into the spherical ball such that contact area between the ball and the bearing segments is maximized. The segments include tapered side walls so as to be mechanically interlocked within the polymeric cup insert, and the bearing surface and its opposing surface are maintained in a substantially parallel orientation with the interior surface of the shell to thereby produce a more uniform transfer of mechanical stress in order to further inhibit wear debris generation.

Polymer wear at the socket-ball articulating interface may be eliminated, or at least significantly reduced by using wear-resistant bearing surfaces of the socket component which are raised above the surface of the polymeric cup insert. The raised bearing surfaces prevent contact between the ball component and the polymeric cup insert. Therefore, bearing segments are preferably embedded in the polymeric cup insert of the present prosthetic joint implant resulting in a composite system. By raising the bearing surfaces of each segment above the polymeric material, channels may be formed between the segments which aid in the lubrication of the bearing couple by providing synovial fluid to the bearing surfaces and thereby reducing frictional torque and resulting accelerated wear. As a result of the teachings of the present invention, the generation of polymer wear debris at the interface between the polymeric cup insert and the metal shell is also eliminated, or at least significantly reduced.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 5 is fragmented, cross-sectional view of the polymeric cup portion of the prosthetic hip joint of FIGS. 1–4, showing one of the ceramic segments embedded therein;

FIG. 6 is a side, cross sectional view of a hemispherical mandrel used in the manufacture of the socket of FIG. 2;

FIG. 6A is a side view of a hemispherical mandrel used in the manufacture of the socket of FIGS. 1–4;

FIG. 7 is a displacement diagram illustrating the effect of radial deformation of the socket upon bearing surface contact area; and FIG. 8 is a partially cross-sectional side view of an alternative embodiment of the hip ball component of the prosthetic hip joint, made in accordance with the present invention.

DETAILED DESCRIPTION

Figure 1:
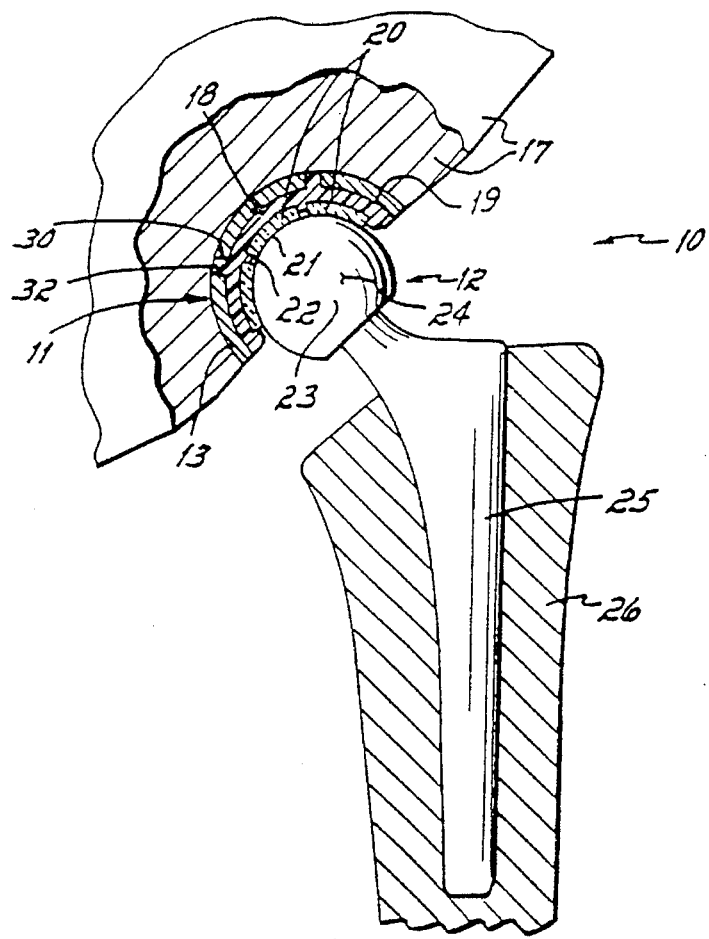
FIG. 1 is a partially cross-sectional, fragmented side view of a prosthetic hip joint made in accordance with the present invention, implanted in a patient.

A preferred embodiment in accordance with the present invention is illustrated in FIG. 1 wherein is shown a hip joint prosthesis 10, with an embodiment of the present invention incorporated therein, including an acetabular socket component 11 in conjunction with a femoral component 12. The socket component 11 includes a hemispherical-shaped metal shell 13 which may be secured within an acetabulum 17 of a patient. The acetabulum 17 is re-sectioned according to convention and the shell 13 is secured therein by standard attachment means such as bone cement, fixation screws, porous coatings, or a combination thereof. The shell 13 is thus a rigid base support structure 13 configured for implanting within a body joint and including a rigid outer surface configured for receiving a bonding agent thereon for securing the base support structure 13 within the joint.

The shell 13 includes a hemispherical interior surface 19 which is lined by a polymeric cup insert 18. The polymeric material used to make cup insert 18 may be, for example, ultra-high molecular weight polyethylene (UHMWPE), medical grade polysulfone, or poly ether ether ketone (PEEK) such as is manufactured by ICI, Exton, Pa., type #450G. The shell may be made of commercially pure (CP) titanium metal or a suitable alloy thereof (e.g. 90% Ti, 6%

Al, 4% V); cobalt-chromium-molybdenum alloys; niobium, tantalum, palladium and their alloys; or other suitable biocompatible materials.

A plurality of bearing segments 20, preferably made from an appropriate ceramic material such as wear resistant alumina, zirconium, or other biocompatible wear resistant ceramics, are embedded in the concave surface of the polymeric cup insert 18, with each segment 20 having an exposed bearing surface 21. The polymeric insert 18 thus resides sandwiched between the segments 20 and the shell 13, and thereby operates as an intermediate cushioning means for transmitting forces between the shell 13 and the segments 20. The segments 20 collectively project outwardly from the polymeric insert 18 and form a discontinuous hemispherical bearing surface, and can be made from any hard and rigid material. The bearing surface 21 of each segment 20 preferably extends above the concave surface of the cup insert 18 such that channels 22 are formed between the segments 20.

The femoral component 12 includes a joint motion surface in the form of a spherically shaped head or ball element 23, preferably made from alumina, and a stem element 25. The femoral ball element 23 is dimensioned to fit within the cup insert 18 and is attached to one end of the femoral stem 25. The other end of stem 25 is embedded into the upper end of a femur 26 corresponding to the acetabulum 17. The femoral ball element 23 has a spherical exterior bearing surface 24 which is maintained in slidable contact with the bearing surfaces 21 of the segments 20. The channels 22 allow synovial fluid to flow between the segments 20 in order to lubricate the interface between the bearing surfaces 21 and 24.

The segments 20, as shown, are preferably circular in shape and of the same size. The total discontinuous bearing surface provided by the segments 20 may be less for circular segments as compared to a polygonal shape (such as a combination of pentagonal and hexagonal segments). However, manufacturing cost savings are realized by using a singular sized segment, and the likelihood of stress risers that may occur at the points of each polygonal segment (not shown) are reduced. In addition, the slight reduction in bearing surface area resulting from the use of circular bearing segments does not appear to cause a critical increase in the load each segment 20 bears. Referring momentarily to FIG. 5, stress risers can also be prevented by forming rounded perimeter corners 31 on the segments 20.

Figure 2:
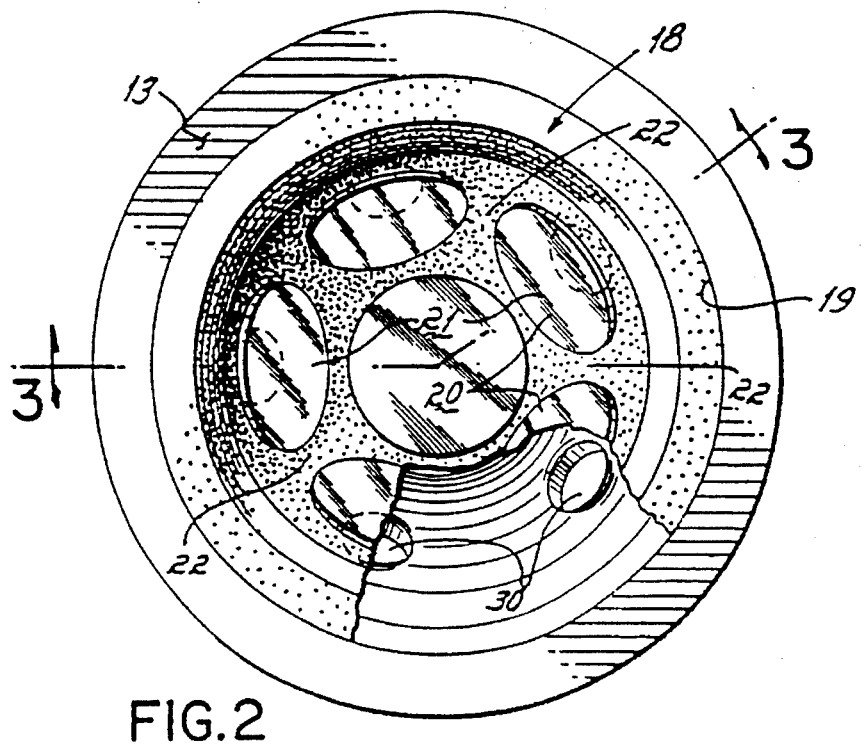
FIG. 2 is a partially fragmented top view of the socket portion of the prosthetic hip joint of FIG. 1.

Referring to FIGS. 1 and 2, in one embodiment of the joint implant 10, the polymeric cup insert 18 and metal shell 13 may be secured in place relative to one another by forming recesses on the inside surface 19 of shell 13, such as a plurality of holes 30 formed through the wall of metal shell 13, and by forming a plurality of matching projections 32 on the convex surface of the cup insert 18. By disposing each projection 32 into its corresponding through hole 30, the cup insert 18 may be locked in place within the shell 13. By precluding relative motion along the interface between the metal shell 13 and the polymeric cup insert 18, micromotion generation of polymeric debris can be eliminated, or at least significantly reduced, thereby reducing the likelihood of osteolysis occurring.

While it is believed that casting, pressing, forging, or other ways of forming cup 18 into the metal shell 13 may be used, the polymeric cup insert 18 is preferably molded into the shell 13 with the shell 13 being a releasable part of the tooling used in the molding process. Injection molding is preferable. However, a compression molding process is preferable if UHMWPE material is used in the molding of the cup insert 18. The tooling used in the molding process is configured to allow insertion and retention of the segments 20 during the molding of the cup insert 18. The plurality of through holes 30 may be used as entrance gates to the mold cavity. Having a plurality of entrance gates, as opposed to one large gate, reduces the force exerted by the molten plastic as it enters the cavity. By reducing this force, the likelihood that the segments 20 will be moved out of position by the flowing molten plastic is reduced.

Figure 3:
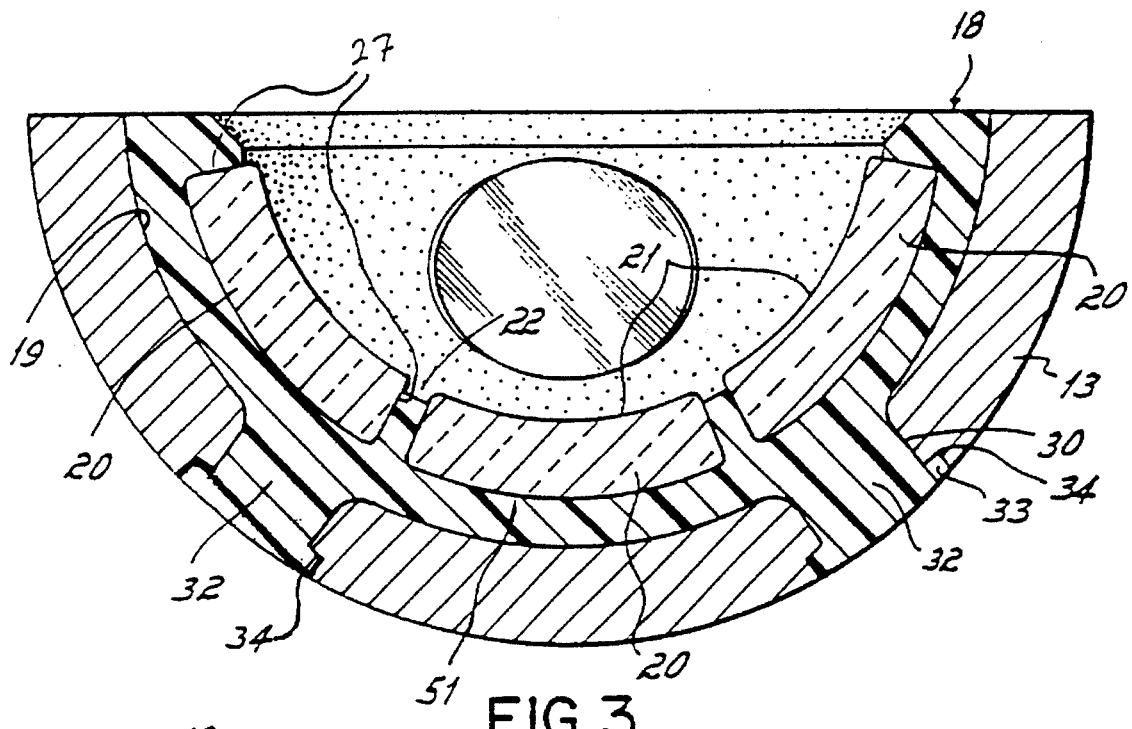
FIG. 3 is a cross-sectional view of one embodiment of the socket of FIG. 2, taken along section 3—3.

Referring to FIG. 3, when through holes 30 are used, it may be desirable to counterbore each hole 30 so as to form an annular shoulder 34 and a corresponding head 33 on each projection 32. Polymeric material often shrinks somewhat as it cures, and it is believed that such shrinkage could be utilized to produce a tensile force within the projections 32. The tensile force causes the heads 33 to seat tightly against the shoulders 34 of the holes 30. In this way, if any wear debris is produced, it will be harder for such debris to exit out any of the through holes 30.

In order to prevent any wear debris that may be produced from passing through the shell 13 and into contact with the acetabulum bone 17, blind holds (not shown) as known in the art may be used instead of through holes 30. With this modification, alternative entrance gates leading into the mold cavity would have to be designed into the tooling. The holes and their matching projections 32 may be other than cylindrically shaped.

Figure 4:
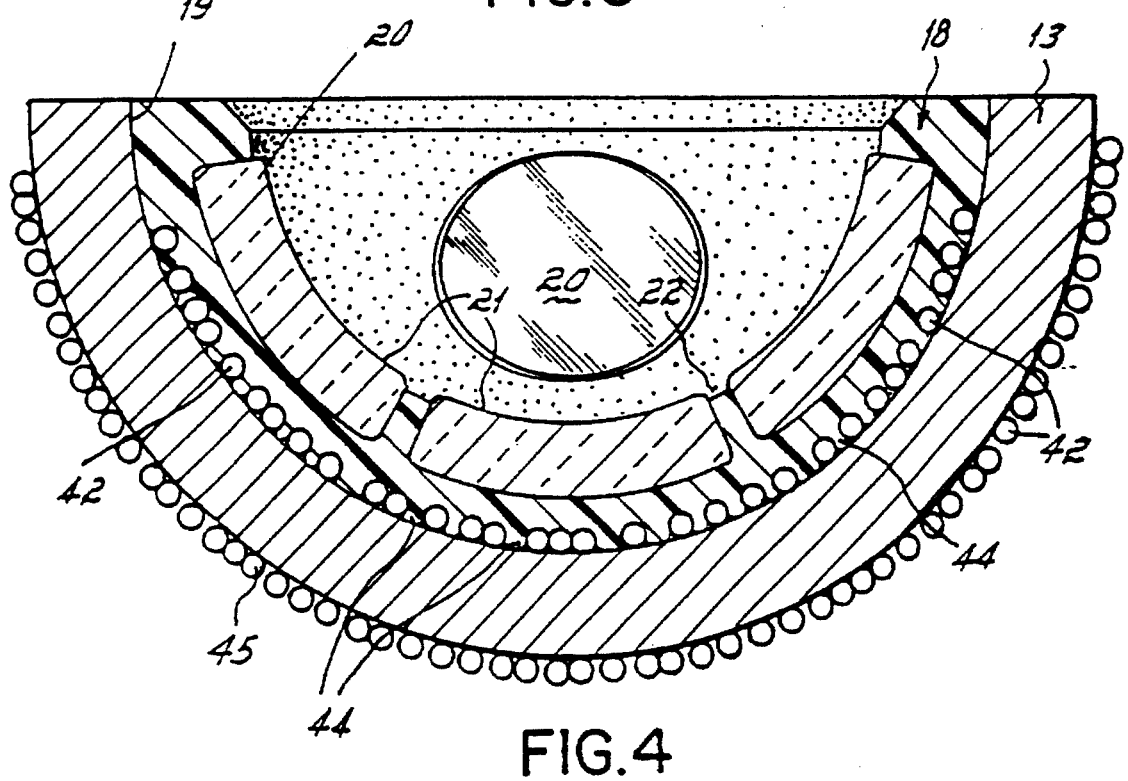
FIG. 4 is a cross-sectional view of another embodiment of the socket of FIG. 2, taken along section 3—3.

Referring to FIG. 4, as an alternative to the use of the through holes 30 or blind holes, the concave surface of the shell 13 may be textured or have a porous coating applied thereto. For example, a plurality of particles such as spherical beads 42 may be integrally joined to shell 13, such as by sintering, plasma spraying, welding or other suitable techniques. With a titanium alloy shell 13, beads 42 are preferably made of CP titanium metal. Thus, when plastic material used to make cup insert 18 is injected into the mold cavity partially formed by shell 13, the polymeric material is forced into pores 44 left between beads 42. With the polymeric material located in pores 44, the cut insert 18 becomes significantly, if not completely, immobile relative to the shell 13. With the relative immobility of the cup 18 and shell 13, osteolysis causing wear debris is less likely to be generated. In addition to the use of a coating of spherical beads 42 on the concave surface of shell 13, a coating of spherical beads 45 on the convex surface of shell 13 may be used as a means for securing the shell 13 to the acetabulum 17.

For the hip joint implant embodiment 10 of the present invention, high purity alumina is used for the femoral head 23 as well as the bearing segments 20. Alumina purity of 99% or higher may be used in bearing applications, although a purity of 99.5% or higher is preferred for implant bearing applications. Other ceramic materials may be used, provided they meet regulatory and functional requirements. The polycrystalline nature of many ceramic materials provides an inherent micro-porosity. Many ceramic materials may also be deliberately produced with micro-porosity or, if desired, macro-porosity on their outer surfaces or throughout by using sintering techniques. This porosity enables the ceramic bearing surfaces to hold synovial fluid. Lubrication from such synovial fluid helps to decrease torsional stresses and thereby wear of the ceramic segments 20 and head 23. Other materials, such as the ruby material disclosed in British Patent No. 1,527,498 has essentially no porosity, due to its single crystal structure, to hold such synovial lubricating fluid. In general, each of the segments 20 may be produced to near net green shape by ceramic fabrication processes such as green machining, gel molding, injection molding, dye pressing or slip casting. Firing is controlled to relatively standard profiles, within standard ceramic firing kilns or controlled-atmosphere high temperature furnaces.

Wearing of the polymeric cup insert 18 can be minimized by accomplishing a uniform transfer of mechanical stress therethrough. Applicants have found that when the segments 20 are formed such that the surfaces 21 and 51 are parallel to each other, and when the segments are embedded within the cup 18 so as to position the surfaces 21 and 51 parallel to the hemispherical interior surface 19 of the shell 13, load transfer is more uniform. The result of these parallel relationships is that the transfer of mechanical stress from the segments 20 through the cup 18 is more uniform and wear on the cup 18 is thereby reduced.

Side walls 27 of the segments 20 preferably taper outwardly away from the concave bearing surfaces 21 to the opposing convex surfaces 51, such that the opposing convex surfaces have more surface area than the concave bearing surfaces. This configuration enables a reduction in mechanical stress transferred from the bearing surfaces 21 into the polymeric cup insert 18, and enables the cup insert 18 to be formed around the tapered side walls 27 to thereby mechanically interlock the segments 20 within the cup insert.

Wearing of the polymeric cup insert 18 can also be minimized by increasing the surface area of contact between the bearing surfaces 21 and the femoral ball element 23. The polymeric material of the cup insert 18 has elastic memory and a substantially lower elastic modulus than the rigid and hard bearing segments 20 to thereby expand and contract responsive to load transfer between contacting surface portions of the ball element 23. The capacity of the polymeric cup insert 18 to expand and contract substantially prevents development of point contacts between the contacting surface portions of the ball element 23 and the segments 20, such that the overall surface contact area therebetween is increased.

Because of its resilience and lower elastic modulus, the polymeric cup insert 18 flexes as loads are transmitted between the ball element 23 and the bearing surfaces 21 of the segments 20, while the shape of the bearing surfaces 21 remains relatively unchanged. This freedom of movement of the segments, under an applied load, allows for greater contact area between bearing surfaces because the segments 20 as a group are able to conform to the geometry and/or position of the opposing bearing surface 24 of the ball element 23. Thus, rather than having highly localized stress concentrations typically occurring in prior art bearing systems, any applied load is shared by a number of segments 20 which results in lower stress being transferred between contacting bearing surfaces.

Applicants have found that another variable affecting the surface area of contact between the bearing surfaces 21 and the ball element 23 is radial displacement within the segmented socket member 11. Such radial displacement is a function of the underlying thickness of the cup insert 18 which resides sandwiched between the segments 20 and the hemispherical interior surface 19 of the shell 13. The cushion-like elasticity of the polymeric cup 18 reduces the overall stiffness of the prosthesis 10 and produces increased radial displacement, increased displacement of the ball element 23 (ball displacement), and increased bearing surface contact. FIG. 7 is included to illustrate that the bearing surface contact (contact zone) is increased when ball displacement increases.

For example, in a completely rigid and continuous socket, the contact area comprises a point on the surface of the socket in the direction of the load. The pressure at this point is infinitely high since the applied load is distributed over an infinitely small area. Applicants have found that by increasing the capacity for radial displacement within the socket component 11, the surface area of contact between the ball element 23 and the bearing surfaces 21 increases. This is consistent with the fact that the prior art ceramic ball engaging against a continuous (i.e. not segmented) ceramic socket is more susceptible to developing point contacts partly as a result of very small radial displacement within the socket member.

Applicants tested socket components 11 having three different underlying thicknesses of the polymeric cup 18, specifically, 0.5 mm, 2.0 mm and 3.5 mm. Applicants also conducted the testing using both UHMWPE and PEEK for the cup insert 18. The UHMWPE material had an elastic modulus of 690 MPa and a Poisson's ratio between 0.45 and 0.50, and the PEEK had an elastic modulus of 1100 MPa and a Poisson's ratio of 0.24. The sockets tested each had six bearing segments in the configuration and orientation shown in FIG. 2. With increased thickness, there occurred reduced stiffness which led to increased displacement of the ball element 23 and reduced peak pressures. The contact area was increased and average pressure decreased with increased thickness.

However, some cases had greater contact area and less average pressure with 2.0 mm thickness than with 3.5 mm thickness. This might be a result of interactions between disk/matrix springs in sharing the applied load. Applicants therefore feel that a cup insert 18 having an underlying cup thickness of 2.0 mm is optimal in a segmented socket 11 of the configuration and orientation shown in FIGS. 1–4, in that this thickness produces increased bearing surface area contact for some loadings when the UHMWPE and PEEK materials are used, with an optimal range of approximately 1.0 mm to 3.0 mm.

Although the 2.0 mm thickness did not produce increased bearing surface contact area in every case as compared to the 3.5 mm thickness, applicants feel that the 2.0 mm thickness is preferred since it did produce increased bearing surface area of contact in some cases and requires much less material and manufacturing cost. Further, PEEK had increased ball displacement in comparison to UHMWPE. In combination with increased thickness, PEEK had a greater rate of ball displacement with increased thickness. The difference in Poisson's ratio influenced the results more than the change in elastic modulus. The range of head displacement seen in applicants testing for a ceramic segment backed by a polymer component was 3.2 microns (0.5 mm thickness at a ninety-degree load direction relative to the segment) to 16.9 microns (3.5 mm thickness at a thirty-five-degree load direction relative to the segment).

Referring now to FIG. 5, the present invention includes forming at least one dimple 29 in the convex surface 51 of each segment 20. The segments 20 are preferably held close to the interior hemispherical surface 19 of the shell 13 during molding of the cup insert 18, so as to enable projections to form as part of the cup insert and extend into the dimples 29. Engagement of the cup insert 18 within the dimples 29 operates to inhibit movement of the segments 20 relative to the cup insert to further inhibit micromotion therebetween and resulting wear debris generation.

As indicated above, one of the structural novelties of the present invention is the parallelism between the surfaces 21 and 51 of the segments 20 and the hemispherical interior surface 19 of the shell 11. Although the convex surfaces 51 of the segments 20 need not conform to a hemispherical section, such is preferred for a more uniform transfer of mechanical stress within the cup 18 as discussed above. It is also highly preferred that the bearing surfaces 21 of the segments 20 conform to a common hemispherical surface, in the configuration and orientation shown in FIG. 2. As such, it is critical how the segments 20 are positioned during the fabrication process.

Referring now to FIG. 6, applicants have conceived of a novel and advantageous fabrication process whereby the segments 20 are simultaneously positioned inside the shell 11 by means of a hemispherical mandrel 60. The mandrel 60 includes a plurality of positioning cavities 62 formed in its exterior surface for receiving the segments 20 therein. Each cavity 62 is defined by outwardly tapering sidewalls 64 and a bottom surface 66. There are preferably six positioning cavities 62 in the orientation shown in FIG. 6, wherein each cavity spans an angle of approximately fifty degrees with respect to a center point 68 of the hemisphere of the mandrel 60, as shown, with a five degree span separating the closest sidewall portions of adjacent cavities 60 as shown.

Referring to FIG. 6A, six of the segments 20 are placed in the six positioning cavities 62, respectively, by gluing the bearing surfaces 21 of the segments 20 directly to the bottom surfaces 66 of the mandrel 60. Any suitable adhesive, such as conventional super glue, may be used. The mandrel 60 is inserted into the shell component 11 as shown by arrow A, and positioned such that the convex surfaces 51 of the segments 20 are parallel with the hemispherical interior surface 19 of the shell 11, at the spacing desired (preferably 2.0 mm as explained above). Liquified polymer is placed into the shell 11, preferably by injection molding, to surround and harden around the segments 20 as in FIGS. 3–4. The heat released by the liquified polymer operates to melt the glue holding the segments 20 within the mandrel 60, permitting the manufacturer to easily remove the mandrel 60. Thus, the tapered sidewalls 27 of the segments 20 and the correspondingly tapered sidewalls 64 of the cavities 62 provide the advantage of easy removal of the mandrel 60 in additional to a stress reduction within the segments during use, as explained above. As such, the mandrel 60 may be used over and over again.

The mandrel 60 and the method described above enables the segments 20 to be held simultaneously in a fixed orientation with respect to the shell. The mandrel 60 thereby prevents malpositioning of the segments, which results in edge loading of the segments 20 during use and excessive wear of the polymeric insert 18.

A preferred method of manufacturing the hip joint prosthesis 10 in accordance with the present invention includes the steps of:

(a) selecting a spherical mandrel having a plurality of positioning cavities formed in an exterior surface thereof for holding objects therein in a predetermined position;

(b) securing curved, rigid and hard bearing segments within the positioning cavities of the spherical mandrel, each segment having a concave bearing surface;

(c) inserting the spherical mandrel, and thus the bearing segments, into a prosthetic shell means, said shell means having an interior surface defining a generally hemispherical concave receiving cavity, such that each bearing segment is held spaced apart from said interior surface of the shell means by a common distance with the concave bearing surface of each segment being held substantially parallel to the spherical interior surface of the shell means; and (d) forming a polymeric cushion, bonding said cushion to the interior surface of the shell means, and interlocking said cushion around the bearing segments such that said segments are partially embedded within the polymeric cushion in a predetermined pattern with the concave bearing surfaces being exposed within the concave receiving cavity and such that an underlying thickness of the polymeric cushion resides sandwiched between the segments and the interior surface of the shell means, wherein the bearing surfaces have substantially the same degree of curvature and are positioned so as to form a discontinuous hemispherical surface for slidable engagement with the spherical joint motion surface.

Embedding the segments 20 into the cup insert 18 by insert molding is preferred for the hip joint implant embodiment 10 of the present invention, although other methods of assembling the segments 20 and cup 18 may be satisfactory for hip joint and other prosthetic applications. These other assembly methods may include, for example, squeeze forming, platen pressing, press fitting, forging, threading or adhesive bonding. When applicable, the bearing surface 21 of the segments 20 can be finished by grinding, lapping and/or polishing, as appropriate, using well known techniques. While surface finishing is preferably performed on the segments 20 after being set within the polymeric cup insert 18, it may also be acceptable to finish the bearing surface 21 of each segment 20 before assembly within the cup insert 18.

Not only can a hemispherical bearing surface be constructed using the concave surfaces 21 of bearing segments 20, such as the bearing surface of the socket component 11, but the convex surface 51 of such bearing segments 20 may also be used to form a spherical bearing surface such as surface 24 of the femoral head 23, as in FIG. 8. The term "hemispherical" as used herein shall not be limited in meaning to a perfect half-sphere, but shall refer broadly to any partial sphere.

More specifically, the polymeric cup insert 18 of FIGS. 1–5 could be replaced with a polymeric cushion 80 secured about the exterior surface 24 of the ball element 23. The segments 20 would be embedded within the cushion 80 such that the larger convex surfaces 51 are exposed for sliding engagement against a rigid and continuous hemispherical interior surface of the shell component. The segments 20 could be secured into the polymeric cushion 80 using much the same method as described above, except that a concave hemispherical mandrel (not shown) would be used, with positioning cavities formed in an interior surface of the concave hemispherical mandrel for holding the segments 20 stationary with respect to the ball element 23. Again, it is preferred that the surfaces 21 and 51 be parallel to the exterior surface 24 of the ball element 23. Each segment 20 is preferably constructed so that its front and back surfaces 21 and 51 are parallel to each other with the radius of curvature of each segment 20 being equal.

Therefore, a ball and socket prosthetic joint implant can be produced which exhibits the desirable characteristics of segmented ceramic-ceramic bearing surfaces while significantly reducing wear and the generation of wear debris, thereby increasing the life of the joint implant by as much as 3 to 5 times.

It will be appreciated that various modifications and alternative configurations of the exemplary prosthetic hip joint 10 can be made in accordance with the principles of the present invention. Such changes may from time to time be made by those skilled in the relevant arts without departing from the spirit and scope of the invention as defined by the appended claims. Those skilled in the art will appreciate that the scope of the present invention encompasses many combinations and a broad spectrum of features and structures equivalent to those specifically discussed herein. The principles of the invention may thus be used in any setting requiring the advantages thereof. Those having ordinary skill in the field of this invention will appreciate the advantages of the invention and its application to a wide variety of uses, and that objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A prosthetic socket member for use in combination with a spherical joint motion surface to form a prosthetic joint device, said prosthetic socket member comprising:

a rigid base support structure configured for implanting within a body joint and including a rigid outer surface configured for receiving a bonding agent thereon for securing the base support structure within the joint, said base support structure further comprising an interior surface defining a generally hemispherical concave receiving cavity;

intermediate cushioning means comprising a matrix bonded to the interior surface of the base support structure;

a plurality of curved, rigid and hard segments each having a concave bearing surface and an opposing convex surface, said segments being partially embedded within the matrix so as to project outwardly therefrom such that the concave bearing surfaces are exposed within the concave receiving cavity and form a discontinuous hemispherical surface for slidable engagement with the spherical joint motion surface, and such that an underlying thickness of the matrix resides sandwiched between the convex surfaces of the segments and the interior surface of the base support structure;

wherein the concave bearing surface and the opposing convex surface of each segment are substantially parallel to each other and to the interior hemispherical surface of the base support structure and wherein the convex surface resides in substantially continuous contact with the intermediate cushioning means to thereby produce a more uniform transfer of mechanical stress from the segments through the matrix so as to reduce wearing of said matrix.

2. A prosthetic socket member as defined in claim 1, wherein each segment includes tapered side walls tapering outwardly away from the concave bearing surface to the convex surface such that the opposing convex surface has more surface area than the concave bearing surface to thereby reduce mechanical stress transferred from said bearing surface into the matrix, and wherein the matrix is formed around the tapered side walls of the segments to thereby mechanically interlock said segments within the matrix.

3. A prosthetic socket member as defined in claim 1, wherein each segment is circular in shape and includes side walls extending from the concave bearing surface to the opposing convex surface, and wherein at least a portion of the sidewalls of each segment protrudes out of the matrix means so as to define channels between adjacent segments for channeling lubrication fluid to thereby lubricate the discontinuous hemispherical surface and the spherical joint motion surface.

4. A prosthetic socket member as defined in claim 1, wherein each segment includes at least one dimple formed in the convex surface thereof and wherein the matrix includes corresponding projections extending into the dimples to thereby inhibit movement of the segments relative to the matrix.

5. A prosthetic socket member as defined in claim 1, wherein each segment is circular in shape and includes side walls extending from the concave bearing surface to the opposing convex surface, and wherein the side walls and the concave bearing surface of each segment intersect to form a rounded perimeter corner section to thereby inhibit stress risers.

6. A prosthetic socket member as defined in claim 1, wherein the bearing surface of each segment has a round shape to thereby inhibit stress risers.

7. A prosthetic socket member as defined in claim 1, wherein the segments are made of a hard ceramic material which includes inherent micro-pores to enable the concave bearing surfaces to hold lubricating fluid within the pores to thereby decrease torsional stresses between the ceramic segments and the joint motion surface.

8. A prosthetic socket member as defined in claim 1, wherein the segments include pores deliberately formed in the concave bearing surfaces for holding lubricating fluid within the pores to thereby decrease torsional stresses between the segments and the joint motion surface.

9. A prosthetic socket member as defined in claim 1, wherein the underlying thickness of the matrix which is sandwiched between the convex surfaces of the segments and the interior surface of the base support structure is within a range of approximately one millimeter to three millimeters.

10. A prosthetic socket member as defined in claim 9, wherein the underlying thickness of the matrix which is sandwiched between the convex surfaces of the segments and the interior surface of the shell means is approximately two millimeters.

11. A prosthetic socket member as defined in claim 9, wherein the matrix is made from a material selected from the group consisting of ultra-high molecular weight polyethylene (UHMWPE), medical grade polysulfone and poly ether ketone (PEEK).

12. A prosthetic socket member as defined in claim 11, wherein the matrix is made from poly ether ether ketone (PEEK) having an elastic modulus of approximately 1100 MPa and a Poisson's ratio of approximately 0.24.

13. A prosthetic socket member for use in combination with a spherical joint motion surface to form a prosthetic joint device, said prosthetic socket member comprising:

a rigid base support structure configured for implanting within a body joint and including a rigid outer surface configured for receiving a bonding agent thereon for securing the base support structure within the joint, said base support structure further comprising an interior surface defining a generally hemispherical concave receiving cavity;

intermediate cushioning means comprising a matrix bonded to the interior surface of the base support structure;

a plurality of curved, rigid and hard segments each having a concave bearing surface and an opposing convex surface, said segments being partially embedded within the matrix so as to project outwardly therefrom such that the concave bearing surfaces are exposed within the concave receiving cavity and form a discontinuous hemispherical surface for slidable engagement with the spherical joint motion surface, and such that an underlying thickness of the matrix resides sandwiched between the convex surfaces of the segments and the interior surface of the base support structure;

wherein the concave bearing surface and the opposing convex surface of each segment are substantially parallel to each other and to the interior hemispherical surface of the base support structure and wherein the convex surface resides in substantially continuous contact with the intermediate cushioning means to thereby produce a more uniform transfer of mechanical stress from the segments through the matrix so as to reduce wearing of said matrix;

wherein each ceramic segment includes at least one dimple formed in the convex surface thereof and wherein the matrix includes corresponding projections extending into the dimples to thereby inhibit movement of the ceramic segments relative to the matrix.

14. A prosthetic socket member as defined in claim 13, wherein each segment is circular in shape and includes side walls extending from the concave bearing surface to the opposing convex surface, and wherein the side walls and the concave bearing surface of each segment intersect to form a rounded perimeter corner section to thereby inhibit stress risers.

15. A prosthetic socket member as defined in claim 14, wherein the matrix is made from poly ether ether ketone (PEEK) having an elastic modulus of approximately 1100 MPa and a Poisson's ratio of approximately 0.24.

16. A prosthetic socket member as defined in claim 15, wherein the underlying thickness of the matrix which is sandwiched between the convex surfaces of the segments and the interior surface of the rigid base support structure is approximately two millimeters.

17. A prosthetic socket member as defined in claim 16, wherein each segment includes tapered side walls tapering outwardly away from the concave bearing surface to the convex surface such that the opposing convex surface has more surface area than the concave bearing surface to thereby reduce mechanical stress transferred from said bearing surface into the matrix, and wherein the matrix is formed around the tapered side walls of the segments to thereby mechanically interlock said segments within the matrix.

* * * * *